United States Patent [19]

Teich et al.

[11] Patent Number: 5,796,477
[45] Date of Patent: Aug. 18, 1998

[54] ENTANGLED-PHOTON MICROSCOPY, SPECTROSCOPY, AND DISPLAY

[75] Inventors: Malvin Carl Teich, Boston; Bahaa E. A. Saleh, Lexington, both of Mass.

[73] Assignee: Trustees of Boston University, Boston, Mass.

[21] Appl. No.: 807,395

[22] Filed: Feb. 27, 1997

[51] Int. Cl.$^6$ ............................................. G01N 21/63
[52] U.S. Cl. ............................................. 356/318; 356/345
[58] Field of Search ........................... 356/317, 318, 356/417, 345; 250/458.1, 459.1, 461.1

[56] References Cited

PUBLICATIONS

Physics News Update. The American Institute of Physics Bulletin of Physics News, No. 275, Jun. 14, 1996 by Phillip F. Schewe and Ben Stein.

*Primary Examiner*—F. L. Evans
*Attorney, Agent, or Firm*—Samuels, Gauthier, Stevens & Reppert

[57] ABSTRACT

The present invention relates to novel entangled-photon microscopy, spectroscopy and display systems. The systems include a source of light in the form of twin or multiple entangled-photon beams. The systems also include optical components that direct the twin or multiple entangled-photon beams towards a target material. The target material includes emission or indicator means responsive to an energy, which approximately equals the sum of the energies of the entangled photons. The systems may further include imaging means that is sensitive to the response of the target material. The present invention also relates to novel correlated-photon microscopy, spectroscopy and display systems. The present invention further relates to methods of correlated-photon microscopy in which a pump beam of photons is provided. A portion of the pump beam is split into a first beam and a second beam, the beams having corresponding correlated photons. The beams are directed towards a target material, thereby allowing the absorption of correlated-photon pairs at selected and adjustable points in the target material. The target material then emits luminescence or causes an effect, which may be captured by an imaging means.

40 Claims, 4 Drawing Sheets

ENTANGLED-PHOTON MICROSCOPY, SPECTROSCOPY, AND DISPLAY

BACKGROUND OF THE INVENTION

1. Field of the Invention

The present invention generally relates to novel microscopy systems and methods, and more particularly relates to microscopy that uses a nonclassical light source consisting of entangled photon pairs.

2. Description of the Background

Recent developments in the field of microscopy have been aimed at enabling users to examine the three-dimensional structure of specimens. Such developments include the use of fluorescence imaging and make use of classical light sources. The classical light sources include incandescent light, fluorescent light, and laser light. The term laser light will often be used here as a catch-all for all forms of classical light. These sources of light are relatively noisy by virtue of their photons arriving randomly in time and position, thereby limiting the fidelity of the image.

One known microscopy technique is wide-field (WF) fluorescence microscopy. To observe a portion of a specimen applying WF fluorescence microscopy, the user tags some characteristic of the specimen with a fluorophore. Under either scenario, a light source is then directed to the specimen to enable the emission of fluorescence from the marker. The absorption of one photon from the source excites a fluorescing molecule to a higher energy band, from which the emission of one photon of fluorescence occurs. The number of molecules excited per unit time, and therefore the number of fluorescence photons emitted per unit time (which is proportional to the fluorescence intensity), increases linearly with source intensity until a limiting or saturation intensity is reached.

Another microscopy technique, confocal laser scanning fluorescence microscopy (CLSM), applies the principles of confocal microscopy to fluorescence imaging. CLSM directs a beam of laser light onto a small spot within a specimen. A pinhole or slit is placed at the focal plane and between the objective and a detector to ensure that only light originating from a specified region of the specimen reaches the imaging plane. CLSM permits thin optical sections to be imaged from within an intact living fluorescence-labeled specimen without the necessity of slicing the preparation into thin physical sections. A three-dimensional distribution of fluorescent markers can be constructed from a collection of CLSM optical sections, with diffraction-limited spatial resolution.

CLSM, however, suffers from a number of limitations. For example, CLSM is limited in sensitivity and spatial resolution by background optical noise that results from out-of-focus fluorescence. In addition, CLSM causes photobleaching and photodamage throughout the illuminated region. Repeated scans with high-energy optical photons greatly reduce the viability of biological tissues and thereby the available time for studying a given specimen.

A technique that overcomes, to some extent, the foregoing problems is two-photon laser scanning fluorescence microscopy (TPLSM). TPLSM involves the nearly simultaneous absorption of two laser photons, rather than one photon, to achieve fluorescence at a desired wavelength. If two photons from a classical light source accidentally find themselves in the vicinity of a fluorescent probe linked with the specimen, and arrive within a time that is shorter than the fluorophore's intermediate-state lifetime and within the cross-sectional area of the atom, absorption occurs. For example, a fluorophore which is ordinarily excited by one ultraviolet (UV) photon, is instead excited by two coincident infrared (IR) photons, each of double the wavelength. If the IR photons both reach a target point in a fluorophore-tagged specimen within the fluorophore's short intermediate-state lifetime, the aggregate energy of the two photons together is the same as that of one UV photon, and the fluorophore will be excited only at the target point. The fluorescence emission is then detected using conventional means.

Figures 1, 2:
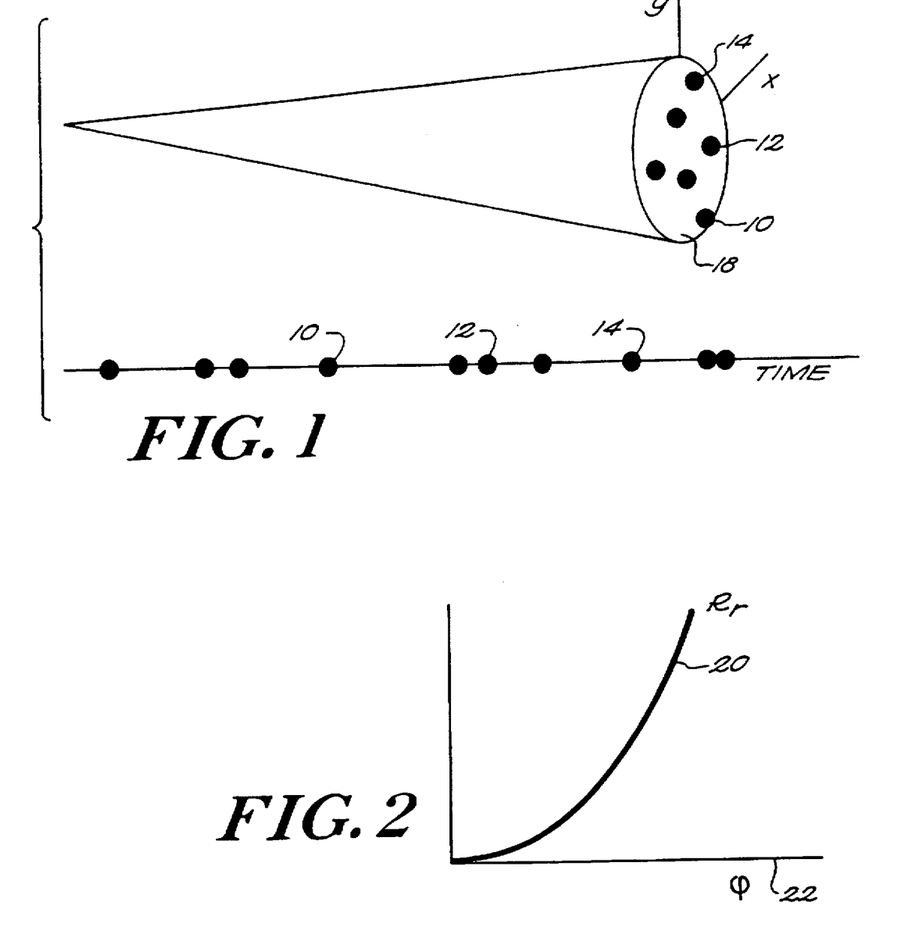
FIG. 1 is a diagram illustrating photon arrivals from a classical light source.
FIG. 2 is a plot of the rate of classical-light two-photon absorption versus the classical-light photon-flux density.

With the classical light sources used in TPLSM, photons arrive randomly and independently following a Poisson point process in time and space, as shown in FIG. 1. Photons 10, 12 and 14 arrive independently in time, as illustrated on the time line 16, and arrive independently in space, as shown in the cross-sectional area 18.

Because the arrival of photons from classical light is purely random, the intensity of the laser must be high enough for two-photon absorption to occur at an acceptably high rate. Relatively large optical powers are required for a photon pair to accidentally arrive within a narrow time window (the intermediate state lifetime), and thereby result in two-photon absorption. Optical excitation in the form of ultrashort (femtosecond) pulses, usually generated by mode-locked lasers, is therefore generally required. Such a light source gives rise to sufficiently large peak powers so that two-photon absorption can occur while maintaining an average light power that is sufficiently low so as to be tolerable to biological specimens. The absorption rate increases, up to a saturation level, as the square of the incident instantaneous laser photon-flux density.

Some advantages of TPLSM derive from the quadratic dependence of the two-photon absorption rate (and thereby the fluorescence intensity) on the instantaneous laser intensity, which is proportional to the incident photon-flux density, $\phi$. When the laser beam is focused, the quadratic dependence results in fluorescence emission that is highly localized in the immediate vicinity of the focal point, where the laser beam is most intense. Fluorescence intensity falls off relatively rapidly in the both the lateral and axial directions, according to the focused shape of the laser beam. Thus, the quadratic dependence gives rise to a sharpening of the active focal region of the excitation light beam. This, in turn, results in an enhancement of resolution in the axial direction and a reduction of background light arising from out-of-focus fluorescence. TPLSM therefore bears some similarities to one-photon (ordinary) CLSM.

At the same time, however, the quadratic dependence of TPLSM leads to inherent limitations of such microscopy systems. For instance, the arrival of pairs of photons at the target specimen is random, and therefore a significant amount of optical power is required to reach an adequate two-photon absorption rate. Photobleaching of the specimen is thus a common occurrence due to the high laser intensity. Also, laser power fluctuations change the size and falloff of the two-photon absorbing region, thereby leading to time-varying resolution and localization. Effects of misalignment errors are similarly exaggerated. Moreover, while more types of fluorophores may be used than with confocal one-photon fluorescence microscopy, the number of available fluorophores is still quite limited.

SUMMARY OF THE INVENTION

The present invention overcomes the problems and disadvantages associated with current microscopy strategies and designs by utilizing a nonclassical light source comprised of entangled photons. Beams of light having highly correlated photon pairs are generated such that the arrival of photon pairs, rather than being accidental, is engineered to occur at a predetermined rate, thereby enhancing the photon-pair absorption rate significantly. This enables lower optical powers to be used, thereby minimizing the effects of photobleaching and photodamage of the material, fluorophore or fluorescence indicator. The absorption of the highly correlated photons depends on the optical intensity of the light source in a linear, rather than quadratic, manner. The linear intensity dependence of two-photon absorption also renders the resolution and localization less sensitive to laser power fluctuations. The effects of misalignment errors are similarly reduced by the present invention. Moreover, the present invention provides a means for dynamic viewing, as a function of real time, in living specimens.

Further, the present invention enables the juxtaposition of the entangled photons to be shifted in time and/or space. Path-delay tuning can be used to create small and adjustable regions in which photon pairs arrive nearly simultaneously, providing enhanced resolution (width of region of photon simultaneity) and enhanced localization (decay of region of simultaneity with distance) in both the axial and lateral directions. In TPLSM these quantities are determined by the quadratic intensity dependence rather than by the independent control of beams. Thus, background light arising from out-of-focus fluorescence is dramatically reduced relative to TPLSM. The present invention's ability to control the interaction region through the use of two maneuverable beams provides increased flexibility in the selection of desired regions of a specimen, leading to enhanced axial and lateral resolution and built-in three-dimensional scanning capabilities controlled solely by optical components. Moreover, a technique called entanglement-time tuning, in which the entanglement time of the source is deliberately selected to be a certain value or values, can be used to enhance the entangled-photon-pair absorption rate, thereby allowing even lower source intensities to be used. Furthermore, a technique called relative-path-length delay tuning, in which the system is arranged such that the entangled-photon pairs come together with a specified delay time relative to each other, can be used, sometimes in conjunction with entanglement-time tuning, to enhance the entangled-photon-pair absorption rate.

One embodiment of the invention is directed to an entangled-photon microscopy system in which the entangled photon pairs are generated in the form of two beams, where each twin beam contains corresponding daughter entangled photons. Optical components direct the twin beams to come together at a particular point within a target material so that entangled-photon pairs are absorbed by the target material. Because each photon of the pair comes from a different optical beam, the entanglement volume location in the specimen is adjustable, thereby providing an additional measure of control for selecting the location and size of the sample region desired. The beam-directing optical components may be arranged such that the twin beams come together in a time-adjusted manner, and/or come together in a space-adjusted manner. This permits three-dimensional scanning to be achieved by the use of beam-directing optical components without the need for mechanical scanning apparatuses. Upon absorption of the entangled-photon pairs, the target material emits fluorescence. The system may also include an imaging means responsive to the emitted fluorescence to produce an image of the three-dimensional structure of the specimen. The daughter entangled photons may be produced by a variety of processes, including parametric downconversion or cascaded atomic emissions.

Another embodiment of the invention is directed to an entangled-photon microscopy system in which the entangled-photon pairs are generated in the form of multiple beams, with each beam containing corresponding daughter entangled photons, and excitation by the simultaneous absorption of multiple photons. The daughter entangled photons may be produced by a variety of processes, including parametric downconversion or cascaded atomic emissions.

Another embodiment of the invention is directed to an entangled-photon microscopy system in which one or more auxiliary beams are used to further enhance two-photon or multiphoton absorption.

Another embodiment of the invention is an entangled-pair microscopy system, where the entangled pairs may consist of electrons, electron-positron pairs, atoms, molecules, or other coupled entities.

Another embodiment of the invention is an entangled-photon microscopy system in which multiphoton absorption induces an effect that may be detected by an imaging means.

Another embodiment of the invention is a method of entangled-photon microscopy that includes providing a pump light beam comprising a stream of photons, splitting the pump beam into twin entangled-photon beams with each twin beam containing corresponding daughter entangled photons, and directing the twin beams to come together at a particular point within a target material, such that the target material emits fluorescence, serving as a fluorescent indicator. The fluorescence may be detected to produce images of various characteristics of the target material.

Another embodiment of the present invention is directed to a method of entangled-photon microscopy that provides at least one additional auxiliary light beam to interact at the specimen along with the twin beams, facilitating the emission of fluorescence by the target material.

Other embodiments and advantages of the invention are set forth, in part in the description which follows and, in part will be apparent from this description and may be learned from practice of the invention.

DETAILED DESCRIPTION OF THE PREFERRED EMBODIMENTS

As embodied and broadly described herein, the present invention is directed to novel apparatuses and methods for entangled-photon microscopy that generate a plurality of beams of entangled photons, which when brought together at a target material, result in the absorption by the target material of multiple entangled photons. Given the unique nature of the source of entangled photons, absorption of multiple entangled photons may occur at low optical power, thereby providing a system which allows the examination of a wide range of specimens. Low light levels also minimize undesirable photodamage, phototoxicity and photobleaching. These latter effects, which are generally more apparent at high photon energies, are particularly deleterious when sensitive biological specimens are exposed to high light intensities. Low light levels also minimize disturbances of the natural energy levels of the sample, such as those which arise from Stark shifts.

The present invention takes advantage of the distinctions between multiphoton absorption from a classical light source and from an entangled-photon light source. This is most readily explained in terms of the two-photon absorption of entangled-photon pairs although it is understood that the invention more generally applies to multiphoton absorption of multiply entangled photons. The absorption process may be regarded as having two steps: (1) the first photon initiates a transition to an intermediate (real or virtual) state; and (2) the second photon brings about a transition to the final state. Once in the final state, a fluorescence photon may be emitted or some process may be activated.

For randomly arriving photons from a classical source of light, probabilistic analysis yields a transition rate $R_r$ (absorptions per second) that depends only on the material's single-photon cross section $\sigma$ and virtual-state lifetime $\tau$. The probability of arrival of one photon in time $\tau$ and area $\sigma$, having a photon-flux density $\phi$ (photons/sec-m$^2$), equals $\phi\sigma\tau$. The probability of accidental arrival of two photons in time $\tau$ and area $\sigma$ equals $(\phi\sigma\tau)^2$. The resulting rate of classical two-photon absorption is therefore $R_r=\delta_r\phi^2$, where $\delta_r=\sigma^2\tau$. As shown in FIG. 2, the rate of two-photon absorption $R_r$ 20 for a classical light source is dependent on the square of the photon-flux density $\phi$ 22.

Figure 3:
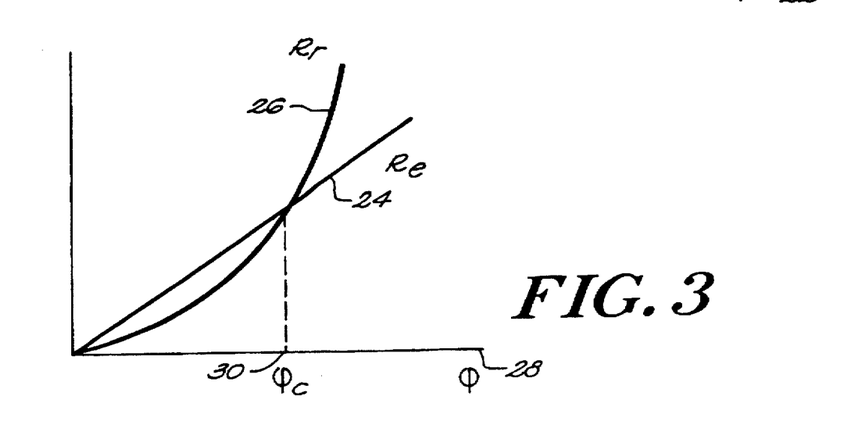
FIG. 3 is a plot of the rate of classical-light two-photon absorption and entangled-light two-photon absorption versus the photon-flux density.

Now consider correlated photon pairs from an entangled-photon source arriving at the absorbing medium with flux density $\phi/2$ photon pairs/sec-m$^2$. In this case, the absorption rate of the material depends on the probability $\xi(T_e)$ that the two photons emitted within the time $T_e$ arrive within $\tau$, and the probability $\zeta(A_e)$ that the two photons emitted within the area $A_e$ arrive within $\sigma$. Thus, the rate of entangled two-photon absorption is $R_e=\sigma_e\phi$, with cross section $\sigma_e=\frac{1}{2}\sigma\xi(T_e)\zeta(A_e)$. If $\tau<<T_e$, $\xi(T_e)$ equals $\tau/T_e$; and if $\sigma<<A_e$, $\zeta(A_e)$ equals $\sigma/A_e$, whereupon the probability of absorption $R_e=\sigma(\tau/T_e)(\sigma/A_e)(\phi/2)$ so that $\sigma_e=\frac{1}{2}(\tau/T_e)(\sigma/A_e)=\delta_r/2A_eT_e$. The entangled two-photon absorption rate $R_e$ must be supplemented by that representing the accidental arrival of pairs within $\tau$ and $\sigma$, resulting in an overall two-photon absorption rate $R=R_e+R_r=\sigma_e\phi+\delta_r\phi^2$. As shown in FIG. 3, the correlated two-photon absorption rate $R_e$ 24 dominates the random two-photon absorption rate $R_r$ 26 for small values of the photon-flux density $\phi$ 28. This is the desired region of operation. The critical photon-flux density 30 at which the two processes are equal is $\phi_c=\sigma_e/\delta_r$.

Figure 4:
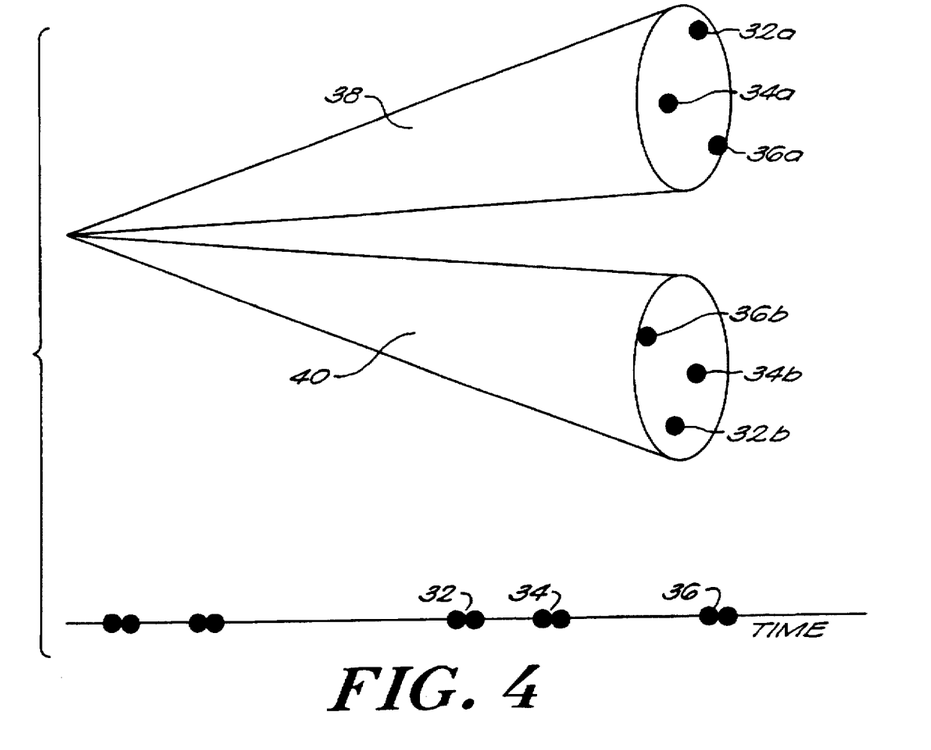
FIG. 4 is a diagram illustrating photon arrivals in twin beams from an ideal entangled light source.

The phenomenon of correlated two-photon absorption may be illustrated by considering an ideal entangled light source. As shown in FIG. 4, photons of an ideal entangled light source arrive in perfect pairs. The two photons of a pair arrive simultaneously, as illustrated on the time line by photon pairs 32, 34 and 36. The two photons of a pair also arrive at matched positions, as illustrated by photons 32a and 32b, 34a and 34b, and 36a and 36b. Each photon-arrival position in the first beam 38 has one and only one corresponding matched photon-arrival position in the second beam 40.

Figure 5:
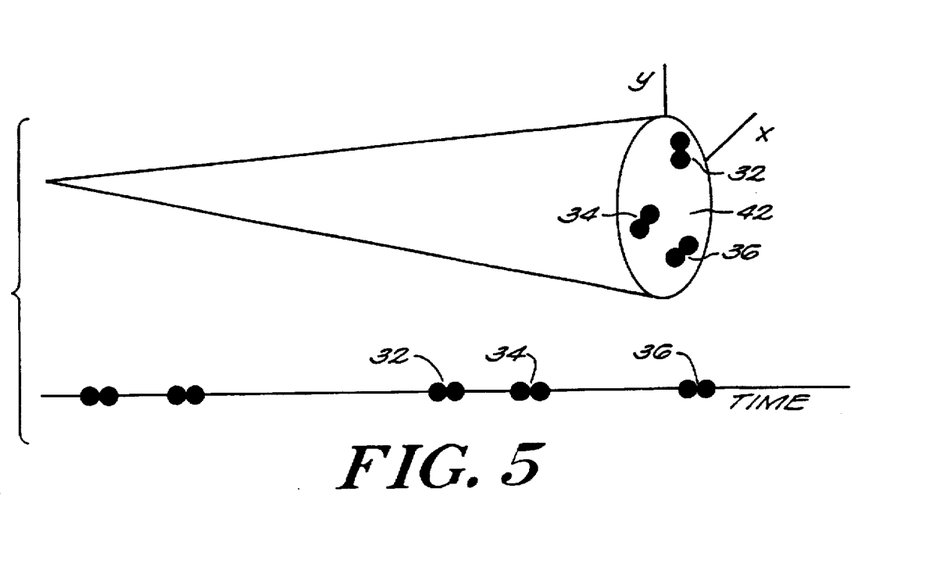
FIG. 5 is a diagram illustrating photon arrivals from an ideal entangled light source using an imaging system.

Using an imaging system, the matching photon pairs can be brought together at a target plane 42 so that they arrive simultaneously at the same position, as shown in FIG. 5. Photon pairs 32, 34 and 36 are matched in time, as illustrated on the time line, and matched in spatial location, as illustrated in the target plane 42.

Figure 6:
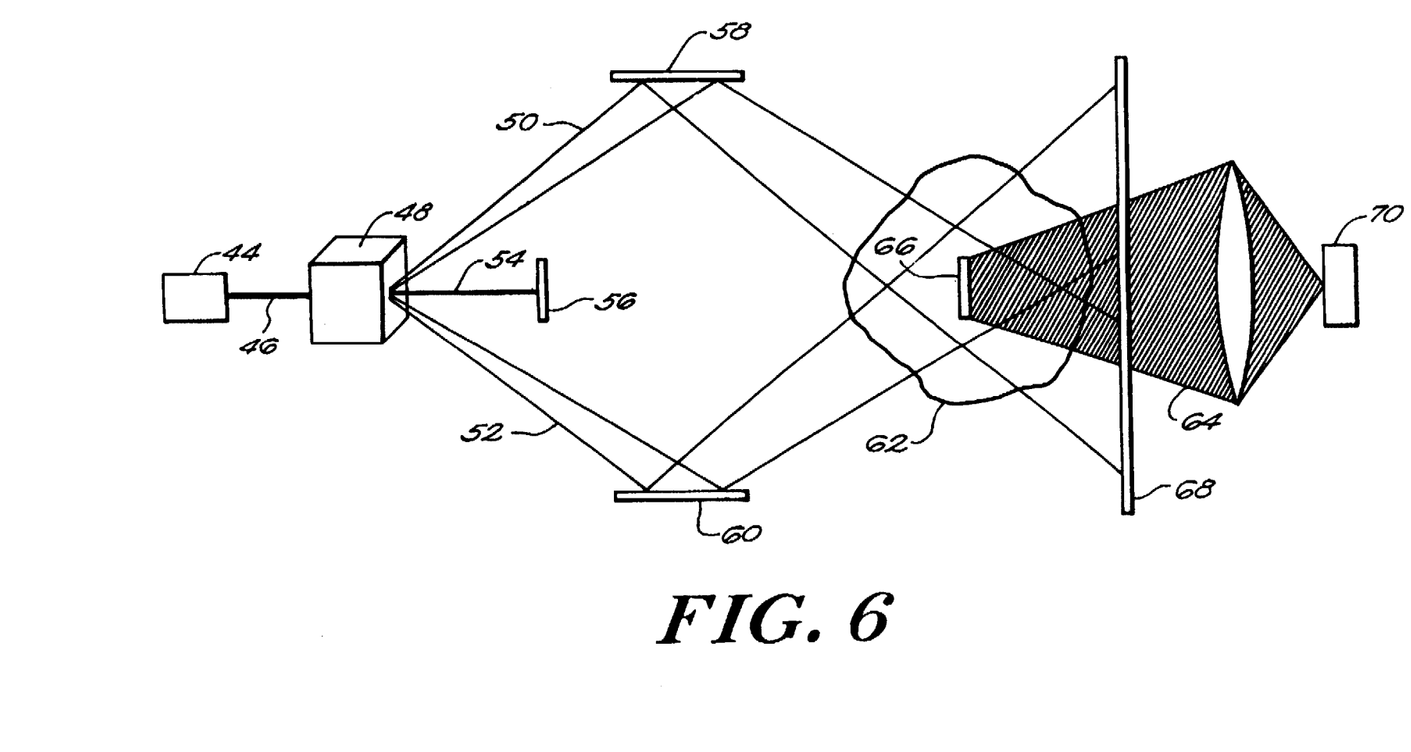
FIG. 6 is a diagram of an entangled-photon microscopy system in accordance with the present invention.

The present invention applies these characteristics of entangled light, but the entangled light need not be ideal. One embodiment of the present invention is shown in FIG. 6. An optical source 44 provides a pump beam 46, which is passed through a nonlinear optical medium 48. The source of the pump beam may be a laser, semiconductor laser, light-emitting diode, incandescent source, or other similar light source. The light source 44 provides light in the form of a beam of photons. The light may be continuous-wave or pulses of, for example, femtosecond or longer duration. The light preferably has energy in the wavelength range from radiowaves to x-rays.

The nonlinear optical medium 48 may be a crystal, a surface, an interface or other similar component. The nonlinear optical medium 48 causes a portion of the pump beam 46 to split into a signal beam 50 and an idler beam 52 (referred to collectively as twin beams), contributing a stream of daughter entangled photons to the signal beam 50 and a corresponding stream of twin daughter entangled photons to the idler beam 52. The signal beam 50 and idler beam 52 may be referred to as entangled-photon beams (also called twin-photon, two-photon, or two-mode squeezed-state beams). The interaction of the pump beam 46 with the nonlinear optical medium 48 generates entangled-photon beams by means of a nonlinear optical process, such as spontaneous parametric downconversion as illustrated, or entangled-photon beams may be generated by other means.

Ideal spontaneous parametric downconversion (SPD) splits each pump-beam photon into twin daughter photons which are emitted simultaneously. Since energy and momentum are conserved in the splitting process, the daughter photons share the energy and momentum of the mother. This entangles the directions of the two daughters so that the emission of one photon in a given direction is associated with an absolutely certain simultaneous emission of a twin photon in a matching direction. The twins may have the same frequency (wavelength or color), in which case they are identical (or degenerate); or differ in frequency (wavelength or color), in which case they are in a sense fraternal (or nondegenerate). The entanglement persists no matter how far away the photons might be from each other. For non-ideal (real) SPD, the emissions are nearly simultaneous (they occur within the entanglement time $T_e$), and the emission of one photon in a given direction is associated with the emission of a twin photon in an area (the entanglement area $A_e$) centered at the matching direction. Thus there is an entanglement volume.

Referring again to FIG. 6, the residual pump photons 54 that fail to be split and thereby to contribute to the signal beam 50 and the idler beam 52 are incident on a filter (or beam dump) 56 that absorbs them. Alternatively they could be re-used by redirecting them back to the nonlinear optical medium 48. The signal beam 50 and the idler beam 52 are then directed towards the specimen 62 by optical components 58 and 60. The optical components may include mirrors, lenses, prisms, gratings, static or dynamic holographic components, graded-index optical components, optical fibers, optical-fiber components or other similar beam-directing mechanisms. The optical components 58 and 60 may be arranged such that an entangled-photon pair arrives within the entanglement volume 66, which can be adjusted to be made small and which lies within a selected portion of the specimen 62. A portion of the specimen 62 then emits fluorescence light 64 at points tagged with a fluorophore when the signal beam 50 and idler beam 52 come together within the entanglement volume 66. Entangled-photon pairs, one from each twin beam, are engineered such that they arrive nearly simultaneously and are absorbed in a specified interaction region, thereby permitting the use of low optical powers. The region of interaction is defined by the optics of the arrangement and by the entanglement volume. The emitted fluorescence light 64, as well as the signal and idler beams 50 and 52, reach a filter 68. The filter 68 absorbs beams 50 and 52, and passes the fluorescence 64. The fluorescence 64 then may be directed by optical components such as lenses to a photodetector 70 where it is detected. The photodetector 70 may be a single detector, an array detector, a CCD or other imaging means.

Figure 7:
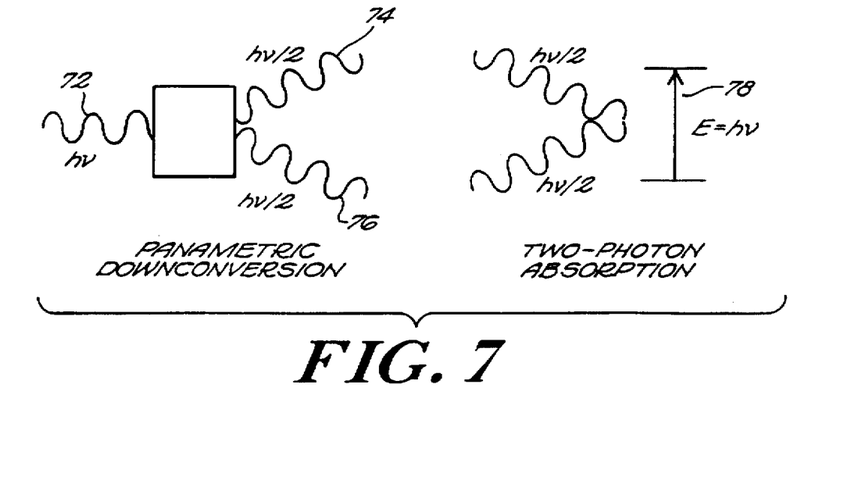
FIG. 7 is a diagram illustrating generation of entangled photon pairs by optical parametric downconversion and two-photon absorption.

Two principal properties of entangled-photon beams are the near coincidence of the emission times of the two streams of photons in two matching directions and the correspondence between each direction in one beam and its matching direction in the other beam. Each beam individually has photons that can arrive randomly in time, and thus exhibits statistical fluctuations (i.e., noise) similar to that of a classical light beam. However, when considering both beams together, the present invention takes advantage of the matching characteristics of the daughter photons. As shown in FIG. 7 for photon-pair generation by means of parametric downconversion, conservation of energy and momentum guarantees this matching of the times and directions of emission of the two entangled photons created from one incoming pump photon. The incoming pump photon 72 has an incoming energy equal to hv. The incoming pump photon is split into two daughter photons 74 and 76 having energies whose sum is hv. In the general nondegenerate case, they split unequally whereas in the special degenerate case depicted in FIG. 7 they split equally so that each daughter photon has energy equal to hv/2. Upon absorption of the daughter photons arriving at the same position of a two-photon absorbing medium, the sum of the energies of the two absorbed daughter photons is hv, matching the energy required for two-photon absorption to occur. Parametric downconversion and two-photon absorption are seen to be dual processes.

One embodiment of the present invention makes use of a light source comprising twin beams of quantum-mechanically entangled photons, which exhibit photon-pair occurrence times that are highly, but not perfectly, correlated. Because energy is conserved in the entangled-pair creation process, the twin photons are produced nearly simultaneously and each has a wavelength longer than the original. Momentum is also conserved, resulting in a nearly one-to-one correspondence between the direction of travel of a photon in one beam and the direction of its matching photon in the other beam. Because they share the energy and momentum of the original photon, the twin photons are said to be "entangled" with each other.

Figure 8:
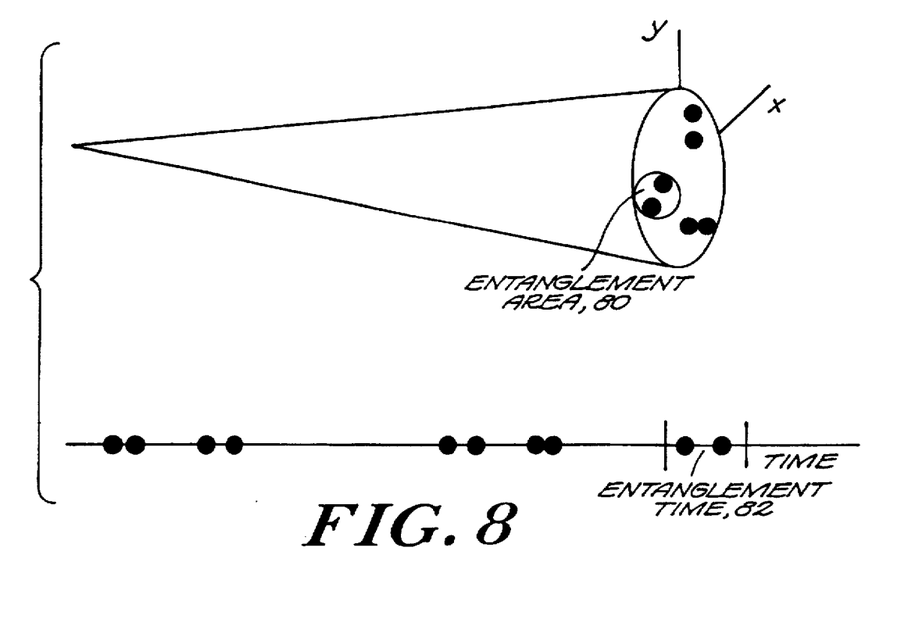
FIG. 8 is a diagram illustrating photon arrivals from a nonideal (real) entangled light source.

The two photons of each pair arrive at random positions within a small area $A_e$, called the entanglement area 80, as shown in FIG. 8. The two photons also arrive at random within a small time interval $T_e$, called the entanglement time 82. The spatial resolution of the system is dependent on, among other things, the entanglement angle. The entanglement angle is the angular width of the cone of directions entangled with one direction of the twin beam. A number of factors influence the size of the entanglement angle, including the spectral width and beam width of the laser, as well as the interaction volume of the nonlinear optical medium. Entanglement angles are typically of the order of tenths of milliradians, so that thousands of independent entangled patches can be used for twin-beam imaging. The temporal resolution of the system is dependent on, among other things, the entanglement time which is typically of the order of picoseconds. Both the entanglement angle and the entanglement time can be adjusted to control the entanglement volume and to optimize system performance.

In other embodiments of the present invention, the entangled-photon beams are generated by processes other than type-I SPD, in which the photons are emitted in separate directions. For example, the beams may be generated by type-II SPD, in which the photons are emitted with different polarizations, either in the same or in different directions. Alternatively, the beams may be generated by SPD in poled or unpoled optical fibers, or at a surface or an interface, or directly at the source or surface of the device producing the pump beam. The beams may be generated by stimulated parametric downconversion or by cascaded atomic emissions, rather than by spontaneous parametric downconversion. With cascaded atomic emissions, a pump beam is incident on a material that emits a cascade of two or more photons, entangled via energy and momentum conservation.

The two beams can be directed by optical components 58 and 60 to intersect with each other in such a way that entangled-photon pairs arrive simultaneously within an arbitrarily selected volume, at an arbitrarily selected position of the specimen. This is called path-delay tuning. One or both of the optical components 58 and 60 are moved or altered so that the position and size of the entanglement region changes. The optical components 58 and 60 may be arranged such that the beams cross at the specimen in a variety of configurations, including at multiple locations. The optical components may be moved mechanically, electrically, acoustically or optically. The moveability of the optical components allows shifting of the focal plane in the transverse (x-y) direction and/or the axial (z) direction. This enables viewing of different locations within a specimen. Regions in which simultaneous photon arrivals occur can therefore be systematically changed by modifying the optical-component position. Accordingly, lateral and axial scanning is achieved optically.

A fluorophore reaches an upper energy level, and emits fluorescence, only when the energy of two daughter entangled photons are combined within a specified lifetime. Prior to absorption of any daughter entangled photons, the fluorophore is in a lower energy state. When a first twin photon reaches the target material, the fluorophore rises to an intermediate (real or virtual) energy state. If the companion entangled photon arrives within a specified time, then the fluorophore is excited to its upper energy state. This upper state may be narrow band. Only at such upper energy level is fluorescence emitted. Therefore, if the arrival of the second twin photon is time-delayed beyond the intermediate-state lifetime, it will not be absorbed in time to cause fluorescence. Accordingly, one can arrange the optical components(s) in such a way that only fluorophores in a limited adjustable region reach the upper energy level and therefore contribute to the fluorescence.

Either or both of the optical components 58 and 60 may also be arranged such that the arrival of twin photons at a given location (or locations) within the specimen occurs with a specified time delay. This is called relative-path-delay tuning. There may be situations where it is desirable for twin photons to arrive at the target material with a specified short relative time delay, which can enhance the two-photon absorption rate and therefore the fluorescence emission rate. By moving or altering at least one of the optical components, the arrival of the twin beam corresponding to the moved optical component(s) can be delayed. The entangled-photon pairs, with relative time delay between their photons, are focused such that a small, but adjustable, region emits fluorescence. This allows the precise targeting of a location within the specimen, and produces a highly localized image of that point.

Pump-beam 46 characteristics such as the spectral width and beam width, and nonlinear-material 48 characteristics such as the crystal length and orientation, can be adjusted to generate entangled-photon beams with adjustable entanglement time. This is called entanglement-time tuning. Certain values of the entanglement time result in an enhancement of the two-photon absorption rate, and thereby the fluorescence emission rate, thus permitting lower pump-beam intensities to be used. This, in turn, can reduce photobleaching, phototoxicity, and photodamage.

Path-delay tuning, relative-path-delay tuning, and entanglement-time tuning can be combined to create small and adjustable regions of the specimen where the two-photon absorption rate, and thereby the fluorescence-emission rate, is optimized. This, in turn, permits optically achieved lateral and axial scanning with enhanced resolution (width of region of effective photon-pair arrivals) and localization (decay of region of effective photon-pair arrivals with distance). In TPLSM these quantities are determined by the quadratic intensity dependence rather than by the intersection of beams. Thus, background light arising from out-of-focus fluorescence is dramatically reduced relative to TPLSM.

In another embodiment of the invention, fluorescence radiation is observed over a range of values of the relative-path-delay and entanglement times, for various values of the path delay. The resulting curves are analyzed by using two-dimensional Fourier or wavelet analysis to provide spectroscopic information about all of the energy levels of the sample that participate in the entangled-photon absorption, simultaneously, at each portion in the specimen. The result is a unique form of spectroscopy of the energy levels of the sample, which we term entangled-photon spectroscopy.

In another embodiment of the invention, one or more pulsed or continuous-wave auxiliary (or control) light beams are directed toward the target material to further enhance two-photon or multiphoton absorption. The sources of the control light beams may be a laser, the fluorescence light itself, or light from other similar devices. This control light serves to couple the initial, intermediate, or final state to other states, thereby enhancing the entangled two-photon absorption rate and/or eliminating undesired transitions. Alternatively, this control light serves as a pump to provide high occupancy of the intermediate state, thereby keeping the material (or fluorophore) in a state of readiness to respond to incoming photons. As one example, three-photon absorption takes place using one photon from the control light together with an entangled pair generated via parametric downconversion.

Another embodiment of the invention employs heterodyning. In this case, light from an auxiliary laser, or other source, impinges on the detector to provide conversion gain and thereby to enhance the detected signal.

In other embodiments of the present invention, nonlinear optical processes are used to generate multiple entangled photons (three, four, and more) in multiple beams. Triples and quadruples of entangled photons are obtained from a higher-order downconverter, from a cascade of two-photon downconverters, or from atomic cascades (for example, an atom cascading through two intermediate levels to produce three entangled photons). Thus, multiphoton (e.g., three-photon) implementations of the invention are possible. These photons are brought together at a specimen, which may be selectively tagged with one or more fluorophores or fluorescent indicators, to produce multiphoton absorption (i.e., absorption of three, four, or more photons) and thence fluorescence from a specimen in a selected entanglement volume.

In yet another implementation of the invention, a pump beam consisting of multiple wavelengths (derived, for example, from the superposition of multiple laser outputs combined at a multiport device such as a beamsplitter) is used to simultaneously excite a number of fluorophores or fluorescent indicators with multiphoton transitions. Each of these different fluorophores acts as an independent marker, tagging a different component or characteristic of the specimen. Fluorescence from the different fluorophores generally exhibits different colors, and thereby is readily distinguished by a color-sensitive detector or imaging system. Moreover, the fluorophores, or indeed natural substances within the specimen itself, may be responsive to different numbers of photons. For example, one fluorophore may respond to two-photon excitation while another responds to three-photon excitation.

Another embodiment of the present invention directs the signal and idler beams to a fourth-order interferometer, such as a beamsplitter or a Mach-Zehnder interferometer. The beam or beams at the interferometer output then impinge on the specimen. One purpose of the interferometer is to provide precise alignment. Another purpose is to reduce the entanglement volume and thereby to improve the image resolution capabilities of the system. As one example, degenerate signal and idle beams are directed to a Hong-Ou-Mandel beamsplitter-interferometer with the path lengths adjusted to provide minimum coincidence for photons emitted from the two output ports of the beamsplitter. The light at either of the beamsplitter output ports then contains a preponderance of entangled photon pairs, so that a specimen placed at one of the output ports automatically, and essentially exclusively, encounters entangled photon pairs. The proportion of entangled photon pairs at the output port is adjustable by modifying the path-length difference of the signal and idler beams before they impinge on the beamsplitter. This configuration obviates the necessity of using crossed signal and idler beams and having to very carefully position the specimen. Furthermore, higher-order multiport beamsplitters (for example, tritters) can be used to produce more than two beams, which would then be subsequently recombined at the specimen.

Another embodiment of the present invention permits dispersive optics and fiber optics to be used. Although it might be desirable to use a pulsed source of entangled photons, the low light levels possible with the present invention enable continuous-wave sources of light to be used. For twin beams that are relatively monochromatic, this can result in a substantial reduction of the deleterious effects associated with dispersive broadening of short optical pulses, and improved beam control. Furthermore, even for nonmonochromatic and pulsed entangled-photon beams, dispersive broadening can be nonlocally canceled by proper choice of optical materials as a result of anticorrelations in the frequency components of entangled photons, engendered by energy conservation. In the case where the twin beams travel through materials having dispersion coefficients approximately equal in magnitude and opposite in sign, for example, the photon arrivals will remain coincident. The present invention can therefore accommodate the use of optical fibers for the transport and processing of light. In TPLSM, in contrast, femtosecond-duration optical pulses are substantially broadened and reduced in magnitude by the dispersion associated with transmission through the microscope's optical components, thereby decreasing the two-photon absorption probability. The optical pulse duration must therefore be chosen to be sufficiently long to avoid this effect in TPSLM. The fact that optical fibers can be used to transport light in the present invention opens the possibility of carrying out near-field entangled-photon microscopy.

Materials with narrow two-photon absorption spectra can be effectively investigated with the present invention because the frequency spectrum of the summed energy of the entangled photon pair is narrow. This, again, results from anticorrelations in the frequency components of the photon pair. In TPSLM, the peak of the material's absorption spectrum must be sufficiently broad to accommodate the spread in the summed energy of the two uncorrelated photons, necessitating the use of optical pulses that are not too short. This restriction is relaxed in entangled-photon microscopy.

The present invention also accounts for the fact that the absorptive properties of a target material depend in a complex manner on the state of the excitation light, including whether the photons are or are not entangled. Although the use of entangled photons has been principally described, the present invention may also use pairs of other entities, such as electrons, electron-positron pairs, atoms, molecules, or photons that are correlated in time and/or space but not necessarily entangled. Examples of the latter include sources of photons that are bunched and/or super-Poissonian, which enhances the rate of multiphoton absorption.

As a result of the entangled nature of the photon pairs, the absorption rate is substantially enhanced and lower levels of optical power can be used for excitation. This approach is particularly useful in biology, where low light levels are often mandatory to avoid damaging specimens. Potential specimens include single atoms, single molecules, atomic clusters, molecular clusters, quantum dots, chromophores, fluorophores, caged compounds, biological molecules, plasma membranes, biological tissues, living neurons, intracellular ions, and intracellular molecules. The ability to control the position of the interaction region by use of two beams provides more flexibility in selecting the desired region than if only a single beam is used, and provides a mechanism for optically implemented three-dimensional scanning. The technique provides higher resolution and better localization than is possible with existing techniques. The present invention also provides a novel optical instrument with the ability to extract ultra low-light-level images from a noisy optical background with a higher accuracy than that afforded by the usual measurement techniques.

Moreover, a wide variety of luminescent or fluorescent materials may be used. The target material may itself be luminescent, or it may contain luminescent means, such as fluorophores or fluorescent indicators. With the present invention, the use of a wide variety of fluorophores and fluorescent indicators becomes possible. Examples of such fluorophores are rhodamine B, fluorescein, indo-1, coumarin, lucifer yellow, and cascade blue. The emitted fluorescence light from a fluorophore or a fluorescent indicator can reveal information about the presence of a material or substance, or about other local ambient conditions such as voltage, current flow, electric field, magnetic field, pH, presence of specific molecules or ions, etc. The final state of the absorbing molecules can have a narrow linewidth. In another implementation, the specimen may itself be a display device, designed to emit multicolor fluorescence in the form of an image, rather than a fluorophore marker or fluorescent indicator representing the presence of a particular characteristic of the specimen.

In addition to fluorescence, any effect induced by multiphoton absorption is contemplated by the present invention. This includes entangled-photon luminescence, entangled-photon photoemission, entangled-photon photoactivation, entangled-photon uncaging, entangled-photon photoacoustic absorption, entangled-photon ionization and entangled-photon localized release of chemicals. For example, by employing entangled-photon photoacoustic absorption, the present invention may be used for measuring small absorption coefficients in gaseous and condensed media, involving the sensing of optical absorption by detecting sound.

In all cases, as with TPSLM, the emitted fluorescence radiation need not be focused, descanned, or passed through special optics, thereby permitting detection to be carried out in more ways than with CLSM. This can be beneficial for imaging in certain media, such as those that scatter light more strongly at shorter wavelengths than at longer wavelengths. Longer wavelength excitation radiation can then reach the interior of a sample while the shorter wavelength emitted fluorescence can be detected over a relatively large solid angle. As an example, entangled three-photon microscopy offers the advantage of longer wavelength excitation, thereby providing access to deeper regions of biological tissue.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. An entangled-photon microscopy system, comprising:
   a source of light, said source of light providing a pump beam of photons;
   a nonlinear optical medium, said nonlinear optical medium receiving said pump beam and splitting a portion of said pump beam into a first twin beam and a second twin beam, wherein daughter entangled photons are contributed to said first twin beam and corresponding daughter entangled photons are contributed to said second twin beam; and
   a plurality of moveable beam-directing components for directing each of said twin beams towards a target material, wherein said target material includes emission means responsive to target excitation.

2. An entangled-photon microscopy system according to claim 1, further comprising detecting means, wherein said detecting means is sensitive to emissions from said target material.

3. An entangled-photon microscopy system according to claim 1, wherein said first and second twin beams are generated by parametric downconversion.

4. An entangled-photon microscopy system according to claim 1, wherein entangled-photon pairs arrive nearly simultaneously at a selected and adjustable small region in said target material, wherein each of said entangled-photon pairs comprises one of said daughter entangled photons and one of said corresponding daughter entangled photons.

5. An entangled-photon microscopy system according to claim 4, wherein said target material is a display device.

6. An entangled-photon microscopy system according to claim 4, wherein said target material releases biological substances via photoactivation.

7. An entangled-photon microscopy system according to claim 4, wherein said target material releases chemicals via photoactivation.

8. An entangled-photon microscopy system according to claim 1, wherein at least one of said moveable beam-directing components is moved mechanically.

9. An entangled-photon microscopy system according to claim 1, wherein at least one of said moveable beam-directing components is moved electrically.

10. An entangled-photon microscopy system according to claim 1, wherein at least one of said moveable beam-directing components is moved acoustically.

11. An entangled-photon microscopy system according to claim 1, wherein at least one of said moveable beam-directing components is moved optically.

12. An entangled-photon microscopy system according to claim 4, wherein the arrival of said entangled-photon pairs is adjusted by path-delay tuning.

13. An entangled-photon microscopy system according to claim 4, wherein the arrival of said entangled-photon pairs is adjusted by relative-path-delay tuning.

14. An entangled-photon microscopy system according to claim 4, wherein the arrival of said entangled-photon pairs is adjusted by entanglement-time tuning.

15. An entangled-photon microscopy system according to claim 4, wherein the arrival of said entangled-photon pairs is simultaneously adjusted by relative-path-delay tuning and entanglement-time tuning.

16. An entangled-photon microscopy system according to claim 15, further comprising Fourier-transform analysis means for providing spectroscopic information.

17. An entangled-photon microscopy system according to claim 1, wherein said beam-directing components include at least one dispersive optical component.

18. An entangled-photon microscopy system according to claim 1, wherein said beam-directing components include at least one graded-index optical component.

19. An entangled-photon microscopy system according to claim 1, wherein said beam-directing components include optical-fiber components.

20. An entangled-photon microscopy system according to claim 1, further comprising at least one auxiliary beam directed towards said target material.

21. An entangled-photon microscopy system according to claim 2, further comprising at least one auxiliary beam directed towards said detecting means.

22. An entangled-photon microscopy system according to claim 1, wherein said pump beam comprises multiple wavelengths.

23. An entangled-photon microscopy system, comprising:
a source of light, said source of light providing a pump beam of photons;
a nonlinear optical medium, said nonlinear optical medium receiving said pump beam and splitting a portion of said pump beam into a plurality of entangled beams; and a plurality of moveable beam-directing components for directing each of said entangled beams towards selected and adjustable points in a target material, wherein said target material includes emission means responsive to target excitation.

24. An entangled-photon microscopy system, comprising:
a source of light, said source of light providing a pump beam of photons;
a nonlinear optical medium, said nonlinear optical medium receiving said pump beam and splitting a portion of said pump beam into a first twin beam and a second twin beam, wherein daughter entangled photons are contributed to said first twin beam and corresponding daughter entangled photons are contributed to said second twin beam;
an interferometer, wherein said interferometer receives each of said twin beams and directs said twin beams towards a target material, said target material including emission means responsive to target excitation; and
detecting means, wherein said detecting means is sensitive to emissions from said target material.

25. A correlated-pair microscopy system, comprising:
a first beam and a second beam, wherein correlated entities are contributed to said first beam and corresponding correlated entities are contributed to said second beam;
a plurality of moveable beam-directing components for directing each of said beams towards a target material, wherein said target material includes emission means responsive to target excitation; and
detecting means, wherein said detecting means is sensitive to emissions from said target material.

26. A correlated-photon microscopy system, comprising:
a source of light, said source of light providing a pump beam of photons;
a nonlinear optical medium, said nonlinear optical medium receiving said pump beam and splitting a portion of said pump beam into a first beam and a second beam, wherein correlated photons are contributed to said first beam and corresponding correlated photons are contributed to said second beam; and
a plurality of moveable beam-directing components for directing said first beam and said second beam towards a target material, wherein said target material includes emission means responsive to target excitation.

27. A correlated-photon microscopy system according to claim 26, wherein said pump beam comprises bunched photons.

28. A correlated-photon microscopy system according to claim 26, wherein said pump beam comprises super-Poissonian photons.

29. A correlated-photon microscopy system according to claim 26, wherein said pump beam comprises multiple wavelengths.

30. A correlated-photon microscopy system according to claim 26, wherein at least one of said moveable beam-directing components is moved mechanically.

31. A correlated-photon microscopy system according to claim 26, wherein at least one of said moveable beam-directing components is moved electrically.

32. A correlated-photon microscopy system according to claim 26, wherein at least one of said moveable beam-directing components is moved acoustically.

33. A correlated-photon microscopy system according to claim 26, wherein at least one of said moveable beam-directing components is moved optically.

34. A correlated-photon microscopy system according to claim 26, further comprising detecting means, wherein said detecting means is sensitive to emissions from said target material.

35. A correlated-photon microscopy system according to claim 26, wherein the arrival of said first beam and said second beam is adjusted by path-delay tuning.

36. A correlated-photon microscopy system according to claim 26, wherein the arrival of said first beam and said second beam is adjusted by relative-path-delay tuning.

37. A correlated-photon microscopy system according to claim 26, further comprising at least one source of auxiliary light directed towards said target material.

38. A correlated-photon microscopy system according to claim 34, further comprising at least one source of auxiliary light directed towards said detecting means.

39. A correlated-photon microscopy system, comprising:

a source of light, said source of light providing a pump beam of photons;

a nonlinear optical medium, said nonlinear optical medium receiving said pump beam and splitting a portion of said pump beam into a first beam and a second beam, wherein correlated photons are contributed to said firm beam and said second beam;

an interferometer, wherein said interferometer receives said first beam and said second beam and directs said first beam and second beam towards a target material, said target material including emission means responsive to target excitation; and a plurality of moveable beam-directing components for directing said first beam and said second beam towards selected and adjustable points in a target material, wherein said target material includes emission means responsive to target excitation.

40. A method of correlated-photon microscopy, comprising the steps of:

providing a pump beam of photons;

receiving said pump beam and splitting a portion of said pump beam into a first beam and a second beam, wherein correlated photons are contributed to said first beam and corresponding correlated photons are contributed to said second beam; and directing said first beam and said second beam towards selected and adjustable points in a target material, wherein said target material includes emission means responsive to target excitation.

* * * * *